United States Patent [19]

De Cueninck

[11] Patent Number: 5,198,215

[45] Date of Patent: Mar. 30, 1993

[54] COMPOSITION FOR CONTROLLING MASTITIS IN RUMINANTS, METHOD FOR ITS PREPARATION AND METHOD OF TREATMENT OF RUMINANTS

[75] Inventor: Bernard J. C. H. De Cueninck, Brugge, Belgium

[73] Assignee: Noordzee Laboratorium N.V., Brugge, Belgium

[21] Appl. No.: 762,726

[22] Filed: Sep. 17, 1991

Related U.S. Application Data

[63] Continuation of Ser. No. 206,887, Jun. 15, 1988, abandoned.

[30] Foreign Application Priority Data

Jun. 22, 1987 [NL] Netherlands .......................... 8701451

[51] Int. Cl.$^5$ ...................... A61K 39/02; A61K 39/40
[52] U.S. Cl. ........................................ 424/92; 424/87; 424/88
[58] Field of Search ................ 424/92, 87, 88

[56] References Cited

U.S. PATENT DOCUMENTS 4,425,330  1/1984  Norcross et al. ..................... 424/92
4,840,794  6/1989  Watson ................................. 424/92

FOREIGN PATENT DOCUMENTS 0041897  12/1981  European Pat. Off. .
200739   7/1986   New Zealand .
8606634  11/1986  PCT Int'l Appl. .
1182555  2/1970   United Kingdom .

OTHER PUBLICATIONS

DeCueninck, et al. *Infection and Immunity*, vol. 41, No. 2 (Aug., 1983).
DeCueninck, *Am. J. Vet. Res.*, vol. 43, No. 9 (Aug. 20, 1981).
Singh, et al. *Jrnl. of Immunology*, vol. 120, No. 3 (Mar., 1978).

*Primary Examiner*—Johnnie R. Brown
*Assistant Examiner*—Abdel A. Mohamed
*Attorney, Agent, or Firm*—Hoffmann & Baron

[57] ABSTRACT

The invention presents a composition for controlling mastitis in ruminants, a method for preparing the composition and a method of treatment of ruminants. The composition contains one or more soluble exoantigens of gram-positive bacteria involved in mastitis, or immunochemical homologues thereof, in a modified form which creates or enhances their ability to induce acquired mammary hypersensitivity. Said composition may be used as a vaccine or as part of a vaccine for ruminants.

4 Claims, 2 Drawing Sheets

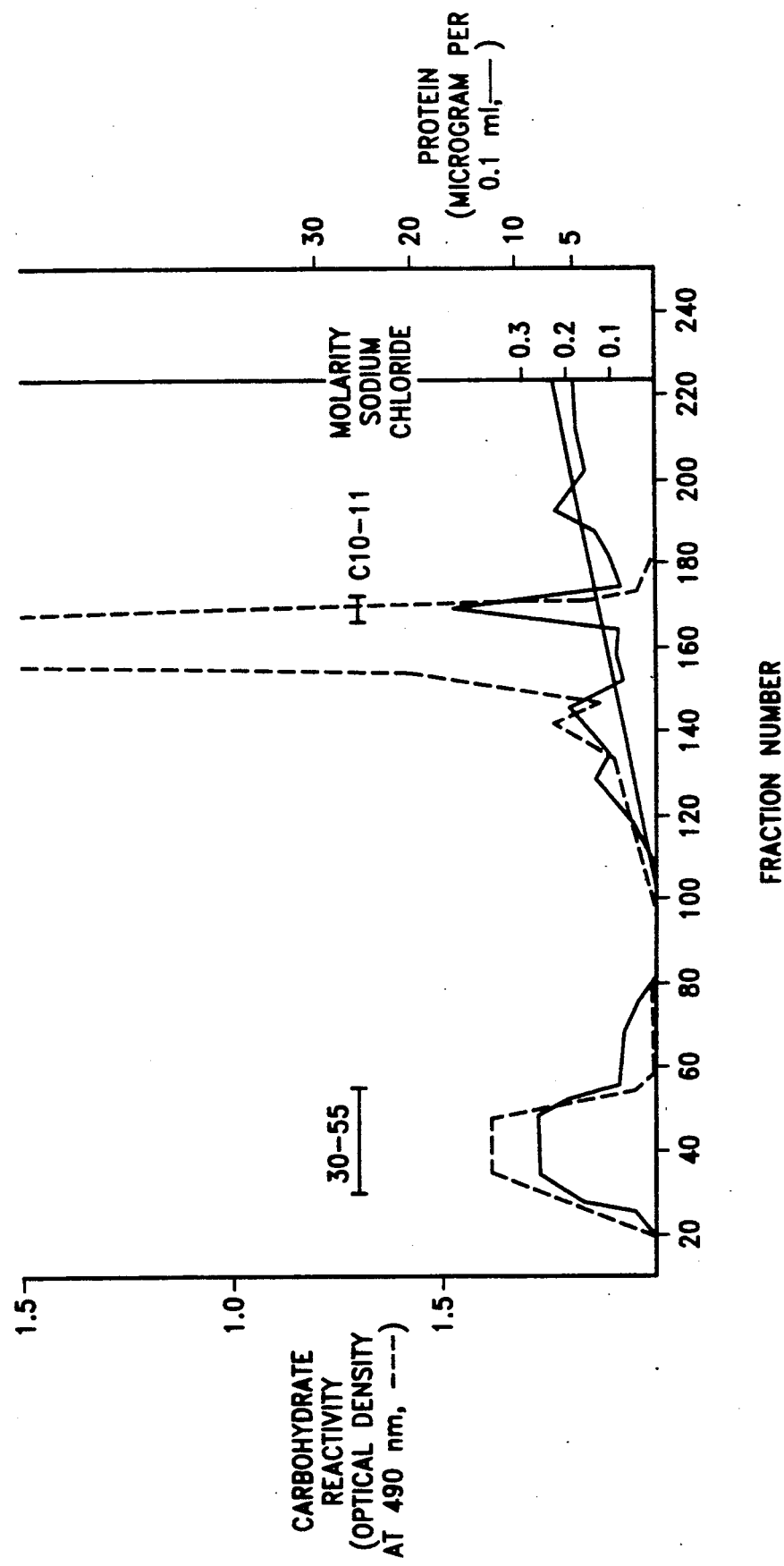

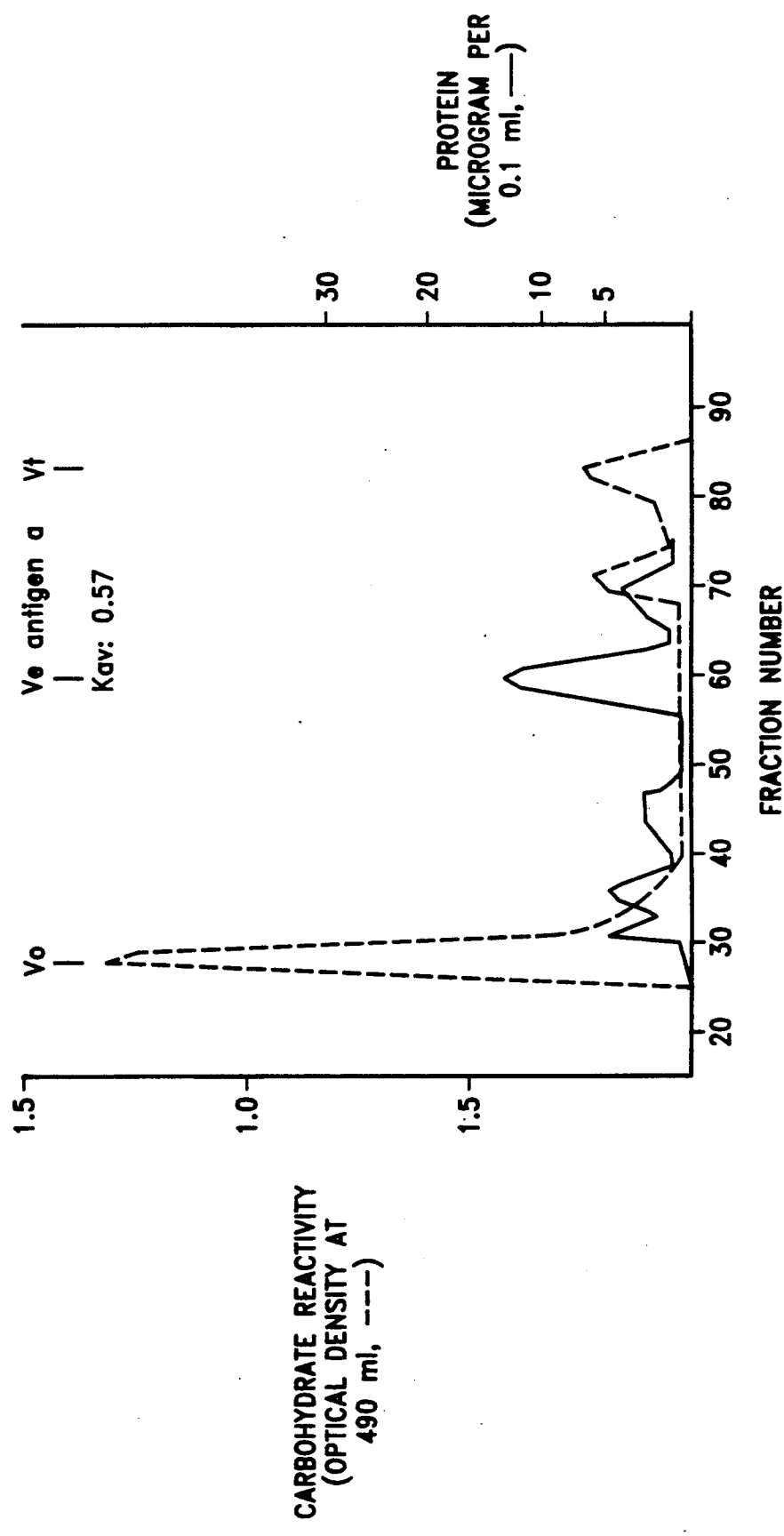
FIG-2 GELFILTRATION CHROMATOGRAM

COMPOSITION FOR CONTROLLING MASTITIS IN RUMINANTS, METHOD FOR ITS PREPARATION AND METHOD OF TREATMENT OF RUMINANTS

This is a continuation of copending application Ser. No. 07/206,887 filed on Jun. 15, 1988, now abandoned.

FIELD OF THE INVENTION

The invention relates to a composition for controlling infectious mastitis (inflammation of the mammary gland) in ruminants such as cattle, sheep, goats, buffalo etc., in which Gram-positive bacteria such as streptococci, staphylococci, corynebacteria, comprising *Str. agalactiae, Str. dysgalactiae, Str. uberis, Str. zooepidemicus, Str. bovis, Staph. aureus*, non-aureus staphylococci, *Corynebacterium pyogenes* etc. are involved. These organisms cause mastitis or act pathogenically in the mammary gland of ruminants; the disease negatively affects the milk yields and quality and the health of the animal and causes large economic losses to the dairy industry and to ruminant production (1,4,5).

BACKGROUND OF THE INVENTION

Mammary infections are initiated when bacteria penetrate a gland via the teat canal and multiply at first in the secretion from where they may eventually invade the mammary tissue. The infections frequently are of chronic nature; the disease often has a subclinical course and clinical flare-ups do occur. Bacterial species and strains endowed with potent toxins cause clinical symptoms more oftenly (1).

Several distinct protective mechanisms of acquired immunity are known to take part in the Gram-positive bacterium—ruminant host interaction; e.g. antitoxin antibody for example induced by a vaccine in which a toxoid is incorporated, attenuates injury caused by bacteria which produce this toxin and aids in preserving the functional integrity of other mechanisms of immunity; the beneficial role of opsonins in the host interaction with Gram-positive bacteria is also firmly established (6, p 627–665) and compositions that induce opsonic immunity contribute relative protection. While the value of the many "conventional" immunities, individually or in combinations, has been documented, the sum of their activities has never been satisfactory when the effect is measured in terms of elimination of existing or challenging infections from the mammary gland.

In vivo killing and elimination of Gram-positive bacteria requires phagocytosis and essential components to be involved in this process (e.g. phagocytes, complement and opsonins) are notoriously absent from the secretion of healthy mammary glands of ruminants or are present in minimal concentrations which do not provide for a major effector capacity. Such effector capacity is necessary whenever bacterial growth escapes other bacteriostatic or bactericidal controls. An efficaceous vaccine, apart from inducing various humoral and cellular immunities, must provide for induction of acquired mammary hypersensitivity (AMH) that permits the immune-mediated recruitment of the essential components whenever anergic immunities fail to contain bacterial growth or to eliminate infections. AMH is an integral part of the immune system of the mammary gland in ruminants and provides for the recruitment function. Indications are that lymphocytes present in mammary secretions and in tissues of specifically sensitized animals, are key mediators of AMH, be it in complex interaction with other cell types and with humoral factors (2,3,7). Homologous antigens can locally elicit recruitment in sensitized animals and mammary functions are normalized shortly after disappearance of the eliciting stimulus.

It therefore has been hypothesized that, if by vaccination, ruminants were made hypersensitive to bacteria, the presence of homologous bacteria in the mammary gland would trigger the recruitment reaction which would be beneficial, particularly in animals having also the other specific immunities such as antitoxic and opsonic immunity.

So far diverse mastitis vaccines and vaccination procedures have been applied or examined in order to control infections by Gram-positive bacteria. Use has been made of diverse bacterial antigen preparations, such as bacterins, cell-lysates, somatic components, toxoids or combinations of these or live attenuated bacteria or inactivated whole bacterial cultures; they have yielded, in some instances, a relative protection, measurable usually in terms of lower frequency and/or lower intensity of clinical disease symptoms rather than in terms of elimination of established or challenging infections and colonizations.

SUMMARY OF THE INVENTION

Mammary infections, artificial interstitial infections with mammary pathogens and antigenically complex vaccines induce non-selectively very diverse immune responses to a variety of bacterial antigens. The responses in some instances include the formation of beneficial opsonins or antitoxins and often also include inefficient, irrelevant and pathogenic humoral and cellular hypersensitivity responses to the same and other antigens, such as the notorious cellular reactions to peptidoglycan and cytophilic antigens. Somatic antigens in particular induce in these circumstances cellular responses and in this context the adjuvant effect of peptidoglycan is known, while soluble exoantigens of the bacteria have humoral immunogenicity only or are even tolerogenic as to cellular immunity or certain immunoglobulin isotypes. These complicated reactions generally enhance the host's susceptibility towards subsequent infections or the pathogenicity of these infections. The pathogenesis of Gram-positive bacterial mastitis originates in part from the direct effects of the microorganisms and in part from acquired immunological reactions to the bacterial antigens (1,8,9,10).

According to the invention it is found that bacterial antigens of a particular group can serve as signals to elicit immune-mediated inflammation (recruitment) that acts only protectively in correctly sensitized animals. The invention thus identifies the antigens or antigenic determinants to be used for AMH induction and reversely, the antigens to be excluded from such use. AMH can be solely protective and non-pathogenic if it is immuno-specific for soluble exoantigens i.e. for antigenic determinants of molecules that, under in vivo conditions, are secreted or released by viable bacteria in soluble form.

Antigens with these characteristics are surprisingly useful as efficient physiological signals in artificially and correctly sensitized animals while somatic antigens and insoluble antigens such as cytophilic antigens and slowly degradable antigenic products such as insoluble peptidoglycans of the bacterial cell wall or e.g. somatic antigens liberated after cell death, or antigenic products deposited in tissues, constitute sources of signals that elicit inefficient acquired hypersensitivity reactions.

BRIEF DESCRIPTION OF THE DRAWINGS

FIG. 1 is an ion exchange chromatogram showing the elution profiles of two soluble protein exoantigens described in Example I.

FIG. 2 is a gelfiltration chromatogram showing the elution profile of a soluble exoantigen fraction described in Example I.

DETAILED DESCRIPTION OF THE INVENTION

Also those soluble exoantigens that not virulence factors and that so far played no role in immunity or that were indirectly pathogenic, e.g. by binding of complement-fixing antibody and complement fixation in previously infected or inappropriately vaccinated animals, appear able to signal the presence of homologous bacteria in the mammary gland following artificial induction of AMH by correct vaccination of the host.

According to the invention, improved vaccines can be designed; vaccine preparations can be composed and formulated to induce AMH that is immunospecific for soluble exoantigens. Such preparations can be integrated in comprehensive vaccines that also induce anergic immunities such as humoral antitoxin- and opsonin-type immunities.

Lymphocytes in complex interaction with other cell types and immunospecific humoral factors form an interaction network for cellular hypersensitivity in general and AMH in particular. Since soluble (non-particulated, non-aggregated, non-cytophilic) antigens that can diffuse freely in body fluids, lack immunogenicity in terms of cell-dependent hypersensitivity, the basis of AMH, and because antigens tend to be tolerogenic in conditions in which they are not immunogenic (6,p 578), cellular hypersensitivity-promoting procedures, formulations and/or adjuvants are to be invoked. Although low concentrations of signal antigen-specific antibodies can have a modulating effector function, e.g. in signal handling in vivo, the use of humoral response oriented procedures, formulations and/or adjuvants is contraindicated; preferential promotion of antibody synthesis tends to selectively inhibit induction of cell-mediated hypersensitivity (6,p 562) and its proper functioning. Vaccination thus must induce a signal antigen-specific immune response that is very different from the humoral response desired towards e.g. toxins and opsoninogens.

The compositions according to the invention consequently contain one or more soluble exoantigens of Gram-positive bacteria involved in ruminant mastitis, or immunochemical homologues thereof, in a modified form that creates or enhances the ability to induce AMH. "Modified" as used herein refers to any suitable form that induces AMH. Suitable forms are for example those with covalently bound lipids or with non-covalently bound ionic surfaceactive products (e.g. for soluble exoprotein antigens); also, the combination of soluble exoantigens with suitable adjuvants, whereby the choice of the adjuvant and of the antigen dose make it possible to avoid the undesired humoral response. The term "immunochemical homologues thereof" refers to parts of exoantigens that carry one or more of the original antigenic determinants, to antigenically homologous structures, and to synthetically prepared molecules that contain an essentially homologous structure.

The water-in-oil emulsions developed by Freund (Freund's adjuvants) are active in ruminants for induction of humoral and of cellular immune responses whereby the dose of incorporated antigen determines the orientation of the response: small doses, in the microgram range for average protein antigens, induce intense cellular hypersensitivity while milligram quantities promote intense antibody formation. Inorganic adjuvants in gel form, alum, aluminum hydroxide, aluminum phosphate, only aid antibody formation and even selectively inhibit induction of cell-dependent hypersensitivities (6, p. 562).

Antigens that in native state induce antibodies and little or no cellular hypersensitivity when administered in soluble form in inert vehicles, can be modified by chemical conjugation, e.g. with lipids (11), to then stimulate selectively hypersensitivity when given in a single microgram dose injection without adjuvant. Ionic surface-active lipids, such as dimethyldioctadecylammoniumbromide, that bind non-covalently to antigens, act similarly. Double conjugation of carrier molecules with e.g. lipids and e.g. antigenic determinants or haptenes, e.g. derived from repetitive soluble exoantigens or other soluble exoantigens that as such are not immunogenic as regards AMH, can yield immunogenic complexes (11,15) that induce AMH which is specific for the original antigens.

The nature and quantities of the soluble exoantigens expressed by bacteria in vivo depend on phase and conditions of life and growth (logarithmic growth, growthstop, unbalanced growth), on the stage of the hostbacterium relationship and on existing immunities of the host. In vivo or, for convenience, in vitro culture conditions can be utilized to produce an exoproduct complex from which relevant antigens to be incorporated in vaccines can be obtained.

The invention permits the development of diverse production methodologies and relevant antigens or antigenic determinants can eventually be obtained through alternative production methods such as organic synthesis and methods involving genetic engineering.

Antigens vary markedly in intrinsic immunogenicity and the optimal dose of any particular antigen, for induction of AMH, depends on its immunochemical nature, on the degree and nature of its eventual derivatization or of the adjuvants used with it, on the ruminant species in which it is to be used, on the route of administration and on other variables.

Variables in the route of antigen administration are known to have bearing on the nature of the resulting immune response. Unresponsiveness, tolerance or split-tolerance in terms of cellular hypersensitivity can result when soluble antigens as such in an inert carrier are administered by the intravenous, peroral, interstitial or intraluminal (in the mammary gland) routes while in contrast the intradermal route generally favors cellular responses. The nature of the chosen adjuvant or build-in adjuvanticity may indicate or limit the choice of the physiologically acceptable routes of administration. So far there is no evidence for the existance of a separate and local, mammary gland-restricted system of AMH in ruminants. The intra-mammary route of vaccine administration can nevertheless be beneficial if compatible formulations and administration schemes are applied.

The set of soluble exoantigens present in total exoproduct, e.g. harvested from in vitro cultures of single bacterial strains and individual soluble exoantigens (e.g. obtained following isolation from exoproduct complexes) can be used to artificially compose vaccines that—as regards specificities and immunogen quantities—are optimal for induction (and later in vivo elicitation during infection) of AMH. The inventive concept also permits soluble exoantigen-vaccine preparations to be artificially optimalized in epidemiological terms: the diversity in immunospecificity of the exoantigens amongst different bacterial strains can fully or in part be accommodated for in one or few vaccines by selectively incorporating shared antigens or by combining two or more genetically independent soluble exoantigens, each representing sets of antigenically different strains or even species.

The antigenic diversity expressed in the functionally different classes of vaccine antigens (signalling antigens, toxins, opsoninogens, etc.) is not necessarily genetically linked and since vaccines for industrial application comprise formulations inducing the diverse immunities, these formulations may be made to differ in antigenic valency.

The inventive concept also applies to the development of compositions for vaccinating infected or previously infected animals with respectively curative and preventive purposes. Genetic engineering involving the signal antigens can also yield useful artificial products such as homologous or heterologous microorganisms able to serve as vaccines that directly induce signal antigen-specific AMH (14).

Ways of carrying out the invention are further explained by examples of application. Applications, equivalent in terms of the inventive concept to the given examples, concern, non-restrictively, the other Gram-positive bacterial species involved in ruminant mastitis, the diverse ruminant species, soluble exoantigens of different chemical nature such as carbohydrates and peptides, and other modifications.

EXAMPLE I

In this application, use is made of *Streptococcus agalactiae* in the bovine model; an isolate, of serotype II, was locally obtained from a naturally infected cow. The semisynthetic medium for which the composition is given in Table A is found suitable for in vitro production of a number of soluble exoantigens. It contains only low-molecular-weight ingredients and consequently allows, following cultivation of bacteria in it and following harvesting of the culture supernatant, the macromolecular bacterial products present to be collected and to be separated from medium ingredients by ultrafiltration and dialysis. In order to obtain soluble exoantigens of lower molecular weight e.g. peptides and saccharides, completely synthetic media and alternative separation methods could be applied.

The organism was cultured in the medium in batches of 10 liters at 37° C. without aeration and the pH of the culture was maintained between 6.5–7.0 by intermittent titration with 8N sodium hydroxide solution. The culture supernatant was harvested in the late logarithmic phase of growth. Ultrafiltration membranes with a nominal molecular weight cut off of 10,000 daltons were used to collect the macromolecular exoantigens and to dialyse the exoproductconcentrate thus obtained. The preparation further designated as Total Concentrate (TC) was prepared by concentrating culture supernatant 100-fold and by dialysing it versus phosphate-buffered saline (0.01 molar sodium phosphate, 0.15 molar sodium chloride, pH 7.00, PBS).

TC, a source of the vaccine antigens to be involved in AMH, was a mixture of exoproducts comprising enzymes, toxins, non-enzymic proteins, nucleic acids, carbohydrates etc. Analysis of TC by means of immunoelectrophoresis, using a number of experimental hyperimmune sera available, revealed the presence of several exoantigens and electrophoretic analysis of TC in protein-denaturing and -dissociating conditions (sodium-dodecylsulfate-polyacrylamide - gelelectrophoresis) followed by coomassie blue staining for protein showed the presence of more than 30 district polypeptides. The antigens of interest according to the invention are defined in physical terms (extracellularity and solubility) and cannot comprehensively be defined in physicochemical terms; the genetically based variation amongst isolates and strains, even within single species, is known to be extensive and dynamic.

From TC, individual soluble exoantigens can be isolated and eventually purified by conventional techniques. Alternatively, undesired products and/or antigens (e.g. cytophilic extracellular lipoteichoic acids) could selectively be removed from TC.

In this example two soluble protein exoantigens, further designated as antigen "a" and as antigen "C10-11" were isolated by means of ionexchange and gelfiltration chromatography. This random choice of vaccine antigens is functionally justified in regard to homologous infectious challenge; for industrial application, epidemiological criteria could be superimposed on the choice.

One hundred ml of TC was dialysed against 0.01 M tris(hydroxymethyl)aminomethane - hydrochloride buffer at pH 7.00 and chromatographed on a column (2.6/30 cm) of diethylaminoethyl-Sephacel (Pharmacia Fine Chemicals, Uppsala, Sweden) in the same medium. The procedure was carried out at 4° C. and 5.40 ml fractions were collected. Unbound components were rinsed through with the same buffer and bound components were eluted by means of a linear NaCl gradient in 0.01 M Tris-HCl buffer pH 7.00. The eluate was monitored for neutral hexose by the phenolsulfuric acid assay of Dubois et al. (12) and for protein by the assay of Lowry et al. (13) using bovine serum albumin as standard. FIG. 1 shows the elution profile obtained. Antigens were traced and identified by immunoelectrophoretic techniques making use of hyperimmune rabbit sera obtained following vaccinations with TC. Antigen a did not bind to the column and appeared in fractions 30–55 and antigen C10-11 eluted from the column in buffer containing 0.13M NaCl.

The antigen C10-11 preparation used for immunizing cattle consisted of the pooled fractions 167–173. This pool contained on a weight basis equal quantities of protein C10-11 and of streptococcal Group B-specific carbohydrate. Antigen a was further purified and characterized by gelfiltration. The fractions 30–55, obtained by ionexchange chromatography, were pooled and concentrated by vacuum evaporation. The concentrate was subjected to chromatography on a column (1.6/94 cm) of Sephadex G75SF (Pharmacia F.C.) in 0.01M sodium phosphate, 1.0 M NaCl, pH 7.00 buffer. The procedure was carried out at 4° C., at a flow rate of 4 ml per hour and fractions of 2.25 ml were collected. The elution pattern obtained is shown in FIG. 2. The average partition coefficient (Kav) of protein a was 0.57. Void volume (Vo) and total volume (Vt) of the column were determined using Blue Dextran 2000 (Pharmacia F.C.) and glucose respectively. The antigen a preparation used for immunizing cattle consisted of a pool of fractions 58-62.

Antigens a and C10-11, in microgram quantities, were incorporated in the incomplete adjuvant of Freund and TC, also in microgram quantities per constituent protein antigen, was incorporated in the complete adjuvant of Freund (Table B). The immunogenicity of the C10-11 preparation and of TC in terms of AMH was thereby restricted to protein antigens and for TC in particular to the proteins present by chance in satisfactory quantities.

The AMH-inducing vaccine preparations were (in the present example) administered subcutaneously to cows that were in late pregnancy or in early lactation and the animals were vaccinated only once.

To test for the acquisition of mammary hypersensitivity following vaccination, antigens a and C10-11, dissolved in 100 microliter of PBS were infused intramammarily at 3 to 5 weeks following immunization. Cows 17 and 18 received 0.5 microgram of antigen a and cows 19 and 20 received 0.5 microgram of protein C10-11 in single glands and cows 23 and 26 received identical doses of both antigens in separate glands. These antigenic challenges elicited early and protracted transient recruitment in the specifically sensitized cows (Nos 17 and 19) and animal 23 reacted to both antigens. The course of the inflammatory reactions was essentially identical to published data (e.g. ref. 2). Control cows were anergic.

The protective value of the induced states of mammary hypersensitivity, being of differing specificities, was revealed by challenging the vaccinated cows with homologous bacteria. Two to six weeks following mammary antigenic challenge, the sensitized and control cows were subjected to infectious challenge in a single gland, (not previously exposed to the bacterial antigens and free of infection and inflammation) by inoculating 70 to 270 colony forming units (CFU, washed and suspended in PBS) of the homologous organism. Tables C, D and E outline the initial courses of the infections and of the host reactions by means of two parameters: the concentrations 1. of bacteria (measured as CFU on sheep blood agar plates) and 2. of polymorphonuclear leukocytes in the mammary secretion. The former parameter reflects the net fate of the inoculated bacterial population and the second parameter reflects the "in se" complex reactions of the hosts. Control cows remained chronically infected and developed chronic mastitis and the sensitized cows all eliminated the infections within 60 hours. The leukocyte profiles reflect the relative anergy of the control cows and the AMH of sensitized cows that mediates the elimination of bacteria. While no other immunities than AMH had been induced (antigen a and the C10-11 preparation were neither toxic nor opsoninogenic and TC was not opsoninogenic either), vaccinated animals were able to eliminate the infections.

The fact that optimal acquired immunity is an integrated function of several immunities (AMH, opsonic immunity, antitoxic immunity etc.) was revealed in the following example of application of the invention. Vaccines for industrial application preferentially will induce comprehensive immunity i.e. AMH and other immunities whereever appropriate, such as opsonic immunity for bacteria having antiphagocytic surface characteristics, antitoxic immunity for bacteria endowed with potent toxins, etc.

EXAMPLE II

Revealing the synergistic effect of opsonic immunity and AMH.

The opsoninogenic activity of the species-specific group B streptococcal carbohydrate was utilized. A covalent conjugate of Group B-specific polysaccharide and rabbit serum albumin (39 oligosaccharide units per albumin molecule), in doses of 1.5 milligram protein, was incorporated in the incomplete adjuvant of Freund (2 ml) and was administered once and subcutaneously to the heifers numbered 1,3 and 4 as outlined in Table F.

Three weeks later cows 1 and 3 were sensitized to the soluble exoantigen a (which was also used in example I) incorporated in the complete adjuvant of Freund (50/μg of exoantigen a in 2 ml of Freund's complete adjuvant). Cow 4 served as control and then received the adjuvant emulsion only. The first inoculation induced an antibody response which was predominantly of the opsonic IgG2 isotype. The second inoculation induced Str. agalactiae-specific AMH. A single gland in each cow was challenged, 16 days after sensitizing cows 1 and 3, with 80 CFU of the homologous Str. agalactiae. The course of the infections is outlined in table F; the data reflect the synergistic effect of opsonic immunity and AMH.

EXAMPLE III

A Lancefield Group C streptococcal isolate, identified as Streptococcus dysgalactiae, was locally obtained from the mammary gland of a naturally infected cow. The organism was cultured in vitro in conditions that were identical to those described in Example I and TC was also obtained by the procedure described in that example. Doses of TC containing 1100 microgram protein in 2 ml PBS were emulsified with equal volumes of the complete adjuvant of Freund and were administered subcutaneously to two heifers in the 8th month of pregnancy. Two control animals received only a PBS-adjuvant emulsion. Twelve weeks following vaccination, the animals were subjected to mammary challenge with 120 CFU of the homologous organism. The course of the infections is outlined in Table G. The data show the anergy and susceptibility to infection of the control animals and the AMH and protection of the sensitized animals. Control cows remained infected throughout the observation period of 2 weeks.

OTHER EXAMPLES

Other examples of application of the invention concern the use in AMH of e.g. the extracellular enzymes and/or toxins of Staphylococcus aureus and of non-aureus staphylococci in particular and of all Gram-positive bacterial species, strains and isolates that cause pathogenesis in the mammary gland of ruminants in general.

The existing knowledge concerning several of these soluble exoantigens (in contrast to antigens a and C10-11 of the previous examples) in terms of their genetically determined incidence and linkage, permits vaccine-antigen sets that are epidemiologically justified to be composed artificially; successfull industrial application of such compositions is relatively independent on diagnostic efforts aimed at identifying the antigenic specificities to be involved in any group or herd of animals.

TABLE A

| Composition of culture medium | |
|---|---|
| | Quantity per liter |
| salt-free acid-hydrolysed casein | 20 gram |
| lactose | 40 gram |
| monobasic potassium phosphate | 440 mg |
| dibasic potassium phosphate.trihydrate | 400 mg |
| ammonium sulfate | 600 mg |
| sodium phosphate | 0.08 molar |
| sodium acetate | 6 gram |
| sodium citrate | 225 mg |
| L-glutamin | 300 mg |
| L-asparagin | 300 mg |
| L-tryptophane | 200 mg |
| L-cystine | 200 mg |
| L-cysteinehydrochloride.monohydrate | 1.3 gram |
| riboflavin | 1.6 mg |
| D,L-panthotenic acid | 3.44 mg |
| thiamine.hydrochloride | 1.6 mg |
| paraaminobenzoic acid | 0.32 mg |
| nicotineamide | 8 mg |
| biotin | 0.04 mg |
| pyridoxamine.dihydrochloride | 4.6 mg |
| folic acid | 0.4 mg |
| adenine.sulfate | 43.5 mg |
| guanine.hydrochloride | 15.5 mg |
| uracil | 12.5 mg |
| magnesium sulfate.heptahydrate | 400 mg |
| sodium chloride | 20 mg |
| ferrous sulfate.heptahydrate | 20 mg |
| manganous sulfate.monohydrate | 15.1 mg |

The aqueous medium was adjusted to pH 7.2 with 8 molar sodium hydroxide solution and was sterilized by filtration.

TABLE B

| Vaccinationscheme | | | |
|---|---|---|---|
| Cow No | Adjuvant | Antigen | Dose |
| 17 | IFA | a | 200 |
| 18 | IFA | control | — |
| 19 | IFA | C10-11 | 230 |
| 20 | IFA | control | — |
| 23 | CFA | total concentrate | 1700 |
| 26 | CFA | control | — |

The antigens, in 2 ml PBS, were emulsified with equal volumes of incomplete (IFA) or complete (CFA) adjuvant of Freund. Doses are expressed in microgram protein, determined according to Lowry et al. and using bovine serum albumin as standard.

TABLE C

| | Infection trial | | | |
|---|---|---|---|---|
| | Cow No. 17: antigen a | | Cow No. 18: control | |
| Time | PMN | CFU | PMN | CFU |
| 0 | 9 | 0 | 0 | 0 |
| 10 | 177 | 1,000,000 | 97 | 54,000 |
| 20 | 54,000 | 860 | 5,900 | 300 |
| 44 | 41,000 | 0 | 443 | 0 |
| 72 | 22,000 | 0 | 44 | 720 |
| 96 | 9,900 | 0 | 257 | 3,480 |

The time is expressed in hours following the intramammary inoculation of bacteria; no milk was withdrawn from the glands before the first sampling time indicated. PMN: number of polymorphonuclear leukocytes (in thousands) per ml of mammary secretion, determined microscopically. Counts below the sensitivity-limit of the method (9000 cells per ml) are indicated by 0. CFU: number of colony forming units of bacteria per ml of secretion, determined on sheep blood agar plates.

TABLE D

| | Infection trial | | | |
|---|---|---|---|---|
| | Cow No. 19: antigen C10-11 | | Cow No. 20: control | |
| Time | PMN | CFU | PMN | CFU |
| 0 | 27 | 0 | 9 | 0 |
| 9 | 80 | 41,000 | 3,989 | 26,600 |
| 20 | 50,000 | 20,000 | 7,545 | 300 |
| 33 | 50,000 | 2,000 | 3,273 | 20 |
| 44 | 43,000 | 20 | 2,198 | 40 |
| 57 | 31,000 | 0 | 62 | 20 |
| 68 | 18,000 | 0 | 35 | 1,640 |
| 92 | 9,400 | 0 | 160 | 100,000 |

Legend: cfr. Table C.

TABLE E

| | Infection trial | | | |
|---|---|---|---|---|
| | Cow No. 23: total concentr. | | Cow No. 26: control | |
| Time | PMN | CFU | PMN | CFU |
| 0 | 0 | 0 | 9 | 0 |
| 12 | 2,243 | 80,000 | 53 | 112,000 |
| 18 | 50,000 | 140 | 638 | 720 |
| 24 | 41,333 | 20 | 576 | 80 |
| 36 | 18,125 | 0 | 860 | 160 |
| 48 | 13,714 | 0 | 230 | 4,800 |
| 60 | 7,200 | 0 | 142 | 10,000 |
| 72 | — | 0 | — | 40,000 |
| 96 | — | 0 | — | 3,840 |

Legend: cfr. Table C.

TABLE F

| | Infection trial | | | | | |
|---|---|---|---|---|---|---|
| | Cow No 1 | | Cow No 3 | | Cow No 4 | |
| Opsonic immunity: | + | | + | | + | |
| AMH: | + | | + | | − | |
| Time | PMN | CFU | PMN | CFU | PMN | CFU |
| 0 | 0 | 0 | 18 | 0 | 9 | 0 |
| 10 | 40 | 14,000 | 210 | 26,000 | 676 | 29,000 |
| 21 | 8,000 | 6,300 | 5,000 | 28,000 | 800 | 22,000 |
| 34 | 7,800 | 280 | 6,000 | 12,000 | 2,100 | 40,000 |
| 46 | 3,200 | 0 | 4,300 | 100 | 480 | 100,000 |
| 58 | 2,840 | 0 | 1,900 | 0 | 2,400 | 25,000 |
| 69 | 1,600 | 0 | 720 | 0 | 850 | 3,420 |
| 83 | 480 | 0 | 390 | 0 | 1,620 | 7,300 |

Legend cfr. Table C.

TABLE G

| | Infection trial | | | | | | | |
|---|---|---|---|---|---|---|---|---|
| | Cow No 1: TC | | Cow No 2: control | | Cow No 3: TC | | Cow No 4: control | |
| Time | PMN | CFU | PMN | CFU | PMN | CFU | PMN | CFU |
| 0 | 18 | 0 | 0 | 0 | 0 | 0 | 9 | 0 |
| 10 | 148 | 4,900 | 110 | 27,000 | 3,840 | 42,000 | 1,400 | 51,000 |
| 22 | 3,700 | 190 | 1,690 | 9,300 | 7,400 | 100 | 760 | 48,000 |
| 35 | 8,400 | 0 | 480 | 1,900 | 1,800 | 2 | 1,800 | 880 |
| 46 | 12,900 | 0 | 1,240 | 340 | 720 | 0 | 1,780 | 21,000 |
| 60 | 4,720 | 0 | 970 | 9,200 | 420 | 0 | 840 | 8,400 |
| 71 | 3,400 | 0 | 1,430 | 7,700 | 540 | 0 | 620 | 9,020 |
| 82 | 1,150 | 0 | 1,210 | 720 | 310 | 0 | 1,800 | 3,700 |

Legend cfr. Table C.

What I claim:

1. A composition for inducing, in ruminants, cell-dependent acquired mammary hypersensitive against Gram-positive bacteria which cause mastitis comprising at least one soluble exoantigen of said bacteria or immunochemical homologue thereof, in a modified form to create or enhance the capacity of said soluble exoantigen to induce cell-dependent acquired mammary hypersensitivity in said ruminants.

2. The composition of claim 1 further comprising an antigen of Gram-positive bacteria which cause mastitis, or an immunochemical homologue of said antigen, in a carrier or adjuvant which serves to induce a humeral or cellular immune response other than cell-dependent acquired mammary hypersensitivity.

3. A method of treatment of ruminants whereby cell-dependent acquired mammary hypersensitivity against a Gram-positive mastitis-causing bacterium is induced, comprising administering to said ruminants a composition comprising at least one soluble exoantigen of said bacterium, or an immunochemical homologue thereof, in a modified form to create or enhance the capacity of said exoantigen to induce cell-dependent acquired mammary hypersensitivity.

4. A composition for inducing, in bovines, cell-dependent acquired mammary hypersensitivity against Gram-positive bacterium which cause mastitis, said bacterium is selected from the group consisting of *Streptococcus agalactia, Staphylococcus aureus* and *Streptococcus dysgalactiae*, comprising at least one soluble exoantigen of said bacterium, or an immunochemical homologue thereof, in a modified form to create or enhance the capacity of said antigen to induce cell-dependent acquired mammary hypersensitivity.

* * * * *